US012611561B2

(12) United States Patent
Anderson et al.

(10) Patent No.: US 12,611,561 B2
(45) Date of Patent: Apr. 28, 2026

(54) BIO-BASED, PFA-FREE FIRE FOAM CONCENTRATE COMPOSITIONS COMPRISING PLANT PROTEINS, SURFACTANTS, ALCOHOLS, AND BUILDERS, PRODUCTION THEREOF, AND USE THEREOF

(71) Applicant: CROSS PLAINS SOLUTIONS, LLC, Dalton, GA (US)

(72) Inventors: Kevin R. Anderson, Cedar Rapids, IA (US); David E. Garlie, Eau Claire, WI (US)

(73) Assignee: Cross Plains Solutions, LLC, Dalton, GA (US)

( * ) Notice: Subject to any disclaimer, the term of this patent is extended or adjusted under 35 U.S.C. 154(b) by 0 days.

(21) Appl. No.: 18/421,188

(22) Filed: Jan. 24, 2024

(65) Prior Publication Data

US 2024/0316380 A1 Sep. 26, 2024

Related U.S. Application Data

(60) Provisional application No. 63/453,908, filed on Mar. 22, 2023.

(51) Int. Cl.
| | |
|---|---|
| *A62D 1/02* | (2006.01) |
| *A62C 99/00* | (2010.01) |
| *C12P 21/06* | (2006.01) |

(52) U.S. Cl.
CPC ........ *A62D 1/0078* (2013.01); *A62C 99/0036* (2013.01); *C12P 21/06* (2013.01)

(58) Field of Classification Search
CPC ........... A62C 5/00; A62C 5/002; A62C 5/008; A62C 5/02; A62C 5/022; A62C 5/024;
(Continued)

(56) References Cited

U.S. PATENT DOCUMENTS 2,269,958 A * 1/1942 Urquhart .................. A62D 1/06
252/3
2,413,667 A * 12/1946 Urquhart .............. A62D 1/0078
252/3
(Continued)

FOREIGN PATENT DOCUMENTS

CN 1341469 A 3/2002
CN 101366469 A * 2/2009
(Continued)

OTHER PUBLICATIONS

Alder-Nissen et al. ("The influence of peptide chain length on taste and functional properties of enzymatically modified soy protein," ACS Publications, Functionality and Protein Structure, 1979, 125-146) (Year: 1979).*
(Continued)

*Primary Examiner* — Matthew R Diaz
(74) *Attorney, Agent, or Firm* — Robinson IP Law, PLLC

(57) ABSTRACT

A PFAS-free fire foam concentrate composition comprising water, a plant-based protein, a surfactant, an alcohol, and a builder. The bio-based content of the PFAS-free fire foam is preferably 80% by weight or greater. There is also disclosed a process to produce the PFAS-free fire foam concentrate composition, and the application of the fire foam concentrate onto a Class A fire or Class B fire.

9 Claims, 5 Drawing Sheets

Providing a PFAS-free bio-based fire foam concentrate composition with a bio-based content of greater than 80% on a dry weight basis, the composition comprising a soy protein flour or meal that has been enzymatically modified with a protease enzyme to a viscosity of less than 2000 cps utilizing spindle #4 at 100 rpm at 40 °C, a mixture of CAPB and SLS surfactants, 1-biobutanol, and a citric acid builder — 400

Mixing the PFAS-free bio-based fire foam concentrate composition with water to form a diluted wetting agent — 402

Directing the diluted wetting agent to a fire to extinguish the fire — 404

(58) Field of Classification Search

CPC ......... A62C 5/027; A62C 31/02; A62C 31/12; A62C 99/00; A62C 99/0009; A62C 99/0036; A62D 1/00; A62D 1/0028; A62D 1/0035; A62D 1/0042; A62D 1/005; A62D 1/0071; A62D 1/0078; A62D 1/0085; C12P 21/00; C12P 21/06

USPC ........................ 252/2, 3; 169/43, 44, 46, 47

See application file for complete search history.

(56) References Cited

U.S. PATENT DOCUMENTS

| | | | | |
|---|---|---|---|---|
| 2,767,141 | A * | 10/1956 | Ratzer | A62D 1/0078 252/3 |
| 4,459,213 | A * | 7/1984 | Uchida | A62D 1/0078 252/2 |
| 4,594,167 | A * | 6/1986 | Kobayashi | A62D 1/0071 252/3 |
| 4,757,007 | A * | 7/1988 | Satoh | C12P 21/06 435/68.1 |
| 10,071,273 | B2 * | 9/2018 | Hansen | A62D 1/0071 |
| 10,328,297 | B2 | 6/2019 | Bowen | |
| 10,434,348 | B2 | 10/2019 | Zhao | |
| 10,518,120 | B2 | 12/2019 | Pai | |
| 11,497,952 | B1 * | 11/2022 | Monfils | A62D 1/0071 |
| 11,673,010 | B2 * | 6/2023 | Monfils | A62D 1/0071 169/47 |
| 11,673,011 | B2 * | 6/2023 | Monfils | A62D 1/0071 252/3 |
| 11,771,939 | B2 * | 10/2023 | Monfils | A62D 1/0071 252/3 |
| 11,865,393 | B2 * | 1/2024 | Monfils | A62D 1/0071 |
| 11,865,394 | B2 | 1/2024 | Conboy | |
| 2010/0196575 | A1 * | 8/2010 | Sanchez | A23L 11/45 426/573 |
| 2012/0135116 | A1 * | 5/2012 | Anderson | C08L 97/02 426/329 |
| 2013/0313465 | A1 | 11/2013 | Podella | |
| 2015/0164968 | A1 * | 6/2015 | Otani | C12P 21/06 435/68.1 |
| 2017/0002295 | A1 | 1/2017 | Arhancet et al. | |
| 2018/0014562 | A1 * | 1/2018 | Yu | A23L 5/20 |
| 2019/0337861 | A1 | 11/2019 | Luthe et al. | |
| 2021/0331017 | A1 * | 10/2021 | Dale | A62D 1/0064 |
| 2023/0271046 | A1 * | 8/2023 | Siem | A62D 1/0071 252/3 |

FOREIGN PATENT DOCUMENTS

| | | | | |
|---|---|---|---|---|
| CN | 104984508 | A * | 10/2015 | |
| CN | 105582636 | A | 5/2016 | |
| CN | 106345095 | A * | 1/2017 | |
| CN | 107050730 | A * | 8/2017 | |
| CN | 108245818 | A | 7/2018 | |
| CN | 108553789 | A * | 9/2018 | |
| CN | 110218757 | A * | 9/2019 | |
| CN | 112746091 | A * | 5/2021 | ............. C12P 21/06 |
| CN | 115120524 | A * | 9/2022 | ............. C12P 21/06 |
| DE | 2025152 | C3 | 1/1979 | |
| GB | 2628947 | A * | 10/2024 | ........... C07C 221/00 |
| JP | 61070947 | A * | 4/1986 | |
| WO | 1997/43012 | A1 | 11/1997 | |
| WO | WO-2023283516 | A1 * | 1/2023 | ........... A62D 1/0071 |
| WO | WO-2024103619 | A1 * | 5/2024 | ............. C12P 21/06 |

OTHER PUBLICATIONS

Bernardi et al. ("Enzymatic modification of soy protein concentrates by fungal and bacterial proteases", JAOCS, vol. 68, No. 2, 1991, 102-105) (Year: 1991).*

Nielsen et al. (Enzymes in Food Technology Textbook, Chapter 6, Enzymic modification of food protein, 2002, 110-143) (Year: 2002).*

Zeng et al. ("Improving the foaming properties of soy protein isolate through partial enzymatic hydrolysis," Drying Technology, 31, 2013, 1545-1552) (Year: 2013).*

Liang et al. ("Modification of soy protein isolates using combined pre-heat treatment and controlled enzymatic hydrolysis for improving foam properties," Food Hydrocolloids, 105, 2020, 105764) (Year: 2020).*

Polymer Foams Stabilized by Particles Adsorbed in the Air/Polymer Interface, Velankar, S.S., et al., Macromolecular Rapid Communications, pp. 1329-1334 (2008).

Getting Personal With Characterization, Duffy. J., Pure/Health, pp. 28-30 (Nov./Dec. 2012).

The Formulation Basics for Personal Cleansers, Arif. S. et al., Pilot Chemical Co. (https://www.happi.com/contents/view_features/2009-09-02/the-formulation-basics-for-personal-cleansers/).

Ultrastable Particle-Stabilized Foams, Gonzenbach, Urs et al., Colloids Communications, pp. 3526-3530 (2006).

Composite Foaming Agents on the Basis of High-Molecular Natural Surfactants, Amankeldi, Fariza et al., Colloids Interfaces, pp. 1-8 (2018).

International Search Report and Written Opinion, corresponding to PCT/US2024/012686, issued Jun. 28, 2024 (21 pages).

* cited by examiner

Providing a PFAS-free bio-based fire foam concentrate composition, comprising water, a plant protein, a bio-based surfactant, an alcohol, and a builder ⎯ 100

Mixing the PFAS-free bio-based fire foam concentrate composition with water to form a diluted wetting agent ⎯ 102

Directing the diluted wetting agent to a fire to extinguish the fire ⎯ 104

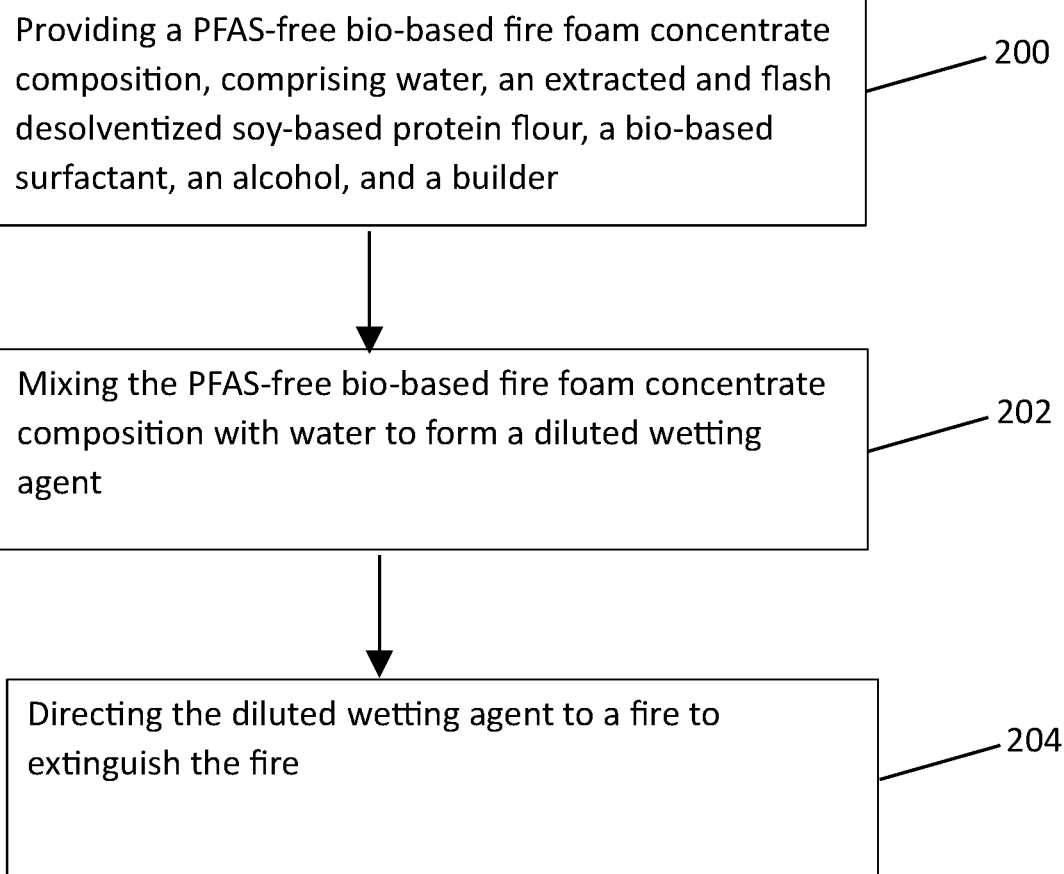

Providing a PFAS-free bio-based fire foam concentrate composition, comprising water, an extracted and flash desolventized soy-based protein flour, a bio-based surfactant, an alcohol, and a builder ⟋ 200

Mixing the PFAS-free bio-based fire foam concentrate composition with water to form a diluted wetting agent ⟋ 202

Directing the diluted wetting agent to a fire to extinguish the fire ⟋ 204

FIG. 3

Providing a PFAS-free bio-based fire foam concentrate composition, comprising water, an extracted and roasted soy-based protein meal, a bio-based surfactant, an alcohol, and a builder — 300

Mixing the PFAS-free bio-based fire foam concentrate composition with water to form a diluted wetting agent — 302

Directing the diluted wetting agent to a fire to extinguish the fire — 304

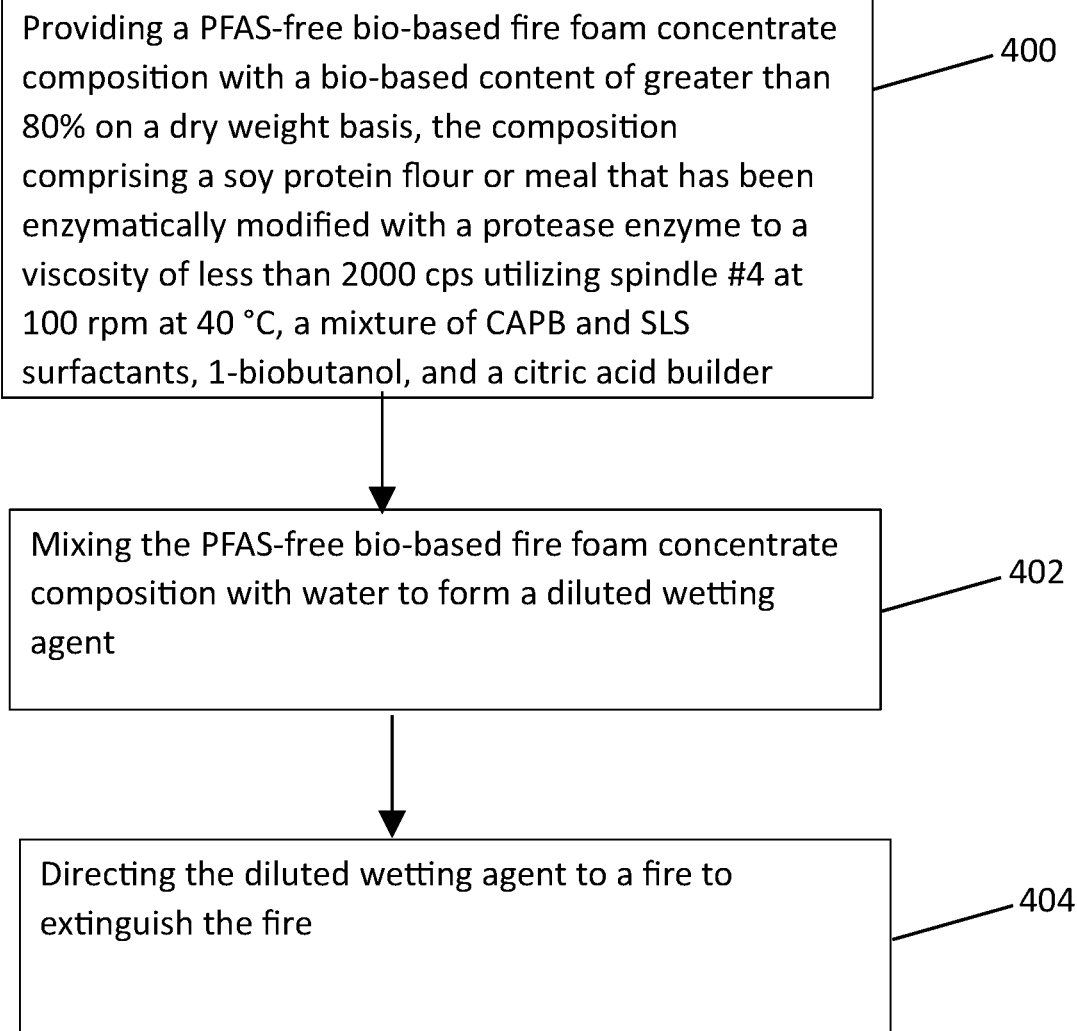

Providing a PFAS-free bio-based fire foam concentrate composition with a bio-based content of greater than 80% on a dry weight basis, the composition comprising a soy protein flour or meal that has been enzymatically modified with a protease enzyme to a viscosity of less than 2000 cps utilizing spindle #4 at 100 rpm at 40 °C, a mixture of CAPB and SLS surfactants, 1-biobutanol, and a citric acid builder — 400

Mixing the PFAS-free bio-based fire foam concentrate composition with water to form a diluted wetting agent — 402

Directing the diluted wetting agent to a fire to extinguish the fire — 404

FIG. 5

BIO-BASED, PFA-FREE FIRE FOAM CONCENTRATE COMPOSITIONS COMPRISING PLANT PROTEINS, SURFACTANTS, ALCOHOLS, AND BUILDERS, PRODUCTION THEREOF, AND USE THEREOF

CROSS-REFERENCE(S) TO RELATED APPLICATIONS

This application claims priority to U.S. Provisional Patent Application Ser. No. 63/453,908 entitled "BIO-BASED, PFA-FREE FIRE FOAM CONCENTRATE COMPOSITIONS COMPRISING PLANT PROTEINS, SURFACTANTS, ALCOHOLS, AND BUILDERS, PRODUCTION THEREOF, AND USE THEREOF" and filed on Mar. 22, 2023, the entire contents of which are incorporated herein by reference.

FIELD OF THE DISCLOSURE

The present disclosure is directed to bio-based, PFAS-free fire foam concentrate compositions comprising a protein, a surfactant, an alcohol and a builder, the process to produce a fire foam concentrate, uses thereof, and materials made using the compositions.

BACKGROUND

Water has long been a universal agent for suppressing fires, but is not best in all cases. For example, water is typically ineffective on oil fires, and can be dangerous by causing further damage. Fire-fighting foams were initially developed for extinguishing Class B oil fires. The concept is to utilize a foam concentrate, typically diluted to a 1% concentration with water by a mechanical proportion inductor, to generate a stable foam that is more effective in suppressing both Class A and Class B fires. It is well known that most of the fire foam concentrates in use today contain PFAS, or polyfluoroalkyl substances, due to its unique ability to vastly reduce the surface tension of the water phase and facilitate penetration of the water into various substrates such as wood products. In Class A fires, defined as ordinary solid combustibles such as paper, wood, cloth and some plastics, increasing the rate of water penetration into the substrate dramatically increases the rate of fire extinction.

PFAS are a group of manmade chemicals used in a vast number of consumer and industrial products. They're often referred to as "forever chemicals," due to their inability to break down under normal environmental conditions. One well-studied PFAS, perfluorooctanoic acid (PFOA), was reviewed by the International Agency for Research on Cancer (IARC) in 2016 and classified as group 2B, a possible human carcinogen. Research links PFAS to other health problems including kidney and testicular cancer, liver and thyroid problems, reproductive problems, pregnancy-induced high blood pressure, low birthweight, and increased risk of birth defects, among others. PFAS has also been linked to changes in cholesterol levels and in the timing of puberty. Over the past few decades there has been increasing pressure to reduce and eventually eliminate the use of PFAS in many industrial processes and products, including the use of PFAS in fire foam concentrate. It is therefore, imperative that PFAS-free fire foam concentrates be developed for their continued use in fire suppression.

SUMMARY OF THE DISCLOSURE

The present disclosure is directed to PFAS-free fire foam concentrate compositions comprising water, plant proteins, surfactants, alcohols, and builders; methods for making such compositions; and methods for using such compositions. "PFAS-free" is defined herein as a composition in which no PFAS is intentionally added to form the composition other than any residual PFAS which might be present in a water source used to supply water for the composition. It is preferable that the PFAS-free fire foam concentrate compositions be derived from bio-based or naturally occurring components wherein the bio-based content of the present disclosed embodiments is greater than 80%. Although bio-based or naturally occurring components are preferably used such as 1-biobutanol, in other embodiments, petroleum-derived butanol may be used. In broader embodiments, the fire foam concentrate compositions are Fluorine-free. "Fluorine-free" is defined herein as a composition in which no Fluorine is intentionally added to form the composition other than any residual Fluorine which might be present in a water source used to supply water for the composition.

In one aspect, a PFAS-free bio-based fire foam concentrate composition is disclosed, the composition comprising water, a plant protein, a bio-based surfactant, an alcohol, and a builder. In some embodiments, the plant protein is a plant protein consisting essentially of a soy-based protein. Preferably, the plant protein has been chemically or enzymatically modified. More preferably, the plant protein has been modified with a protease enzyme. Preferably, the plant protein is a protein comprising a soy-based protein and has been modified with a protease enzyme to a Brookfield viscosity of less than 2000 cps utilizing spindle #4 at 100 rpm at 40° C. Preferably, the plant protein is a protein comprising a soy-based protein and has been modified with a protease enzyme such that the overall composition includes from about 20% to about 80% of plant protein based on the total dry weight of the overall composition. More preferably, the plant protein is a protein comprising a soy-based protein and has been modified with a protease enzyme such that the composition includes from about 50% to about 70% of plant protein based on the total dry weight of the overall composition. In more preferred embodiments of the embodiments described above, the plant protein is a protein consisting essentially of a soy-based protein. For purposes of this disclosure, "consisting essentially of" is defined to mean including at least 95% by weight of a substance or chemical species.

In another aspect, a PFAS-free bio-based fire foam concentrate composition is disclosed, the composition comprising water, an extracted and flash desolventized soy-based protein flour, a bio-based surfactant, an alcohol, and a builder. Preferably, the soy-based protein flour has been chemically or enzymatically modified. Preferably, the soy-based protein flour has been modified with a protease enzyme. In a preferred embodiment, the soy-based protein flour has been modified with a protease enzyme to a Brookfield viscosity of less than 2000 cps utilizing spindle #4 at 100 rpm at 40° C. Preferably, the soy-based protein flour has been modified with a protease enzyme and the overall composition includes from about 20% to about 80% of soy-based protein flour based on the total dry weight of the composition. More preferably, the soy-based protein flour has been modified with a protease enzyme and the composition includes from about 50% to about 70% of soy-based protein flour based on the total dry weight of the composition.

In another aspect, a PFAS-free bio-based fire foam concentrate composition is disclosed, the composition comprising water, an extracted and roasted soy-based protein meal, a bio-based surfactant, an alcohol, and a builder. Preferably, the soy-based protein meal has been chemically or enzymatically modified. More preferably, the soy-based protein meal has been modified with a protease enzyme. In a preferred embodiment, the soy-based protein meal has been modified with a protease enzyme to a Brookfield viscosity of less than 2000 cps utilizing spindle #4 at 100 rpm at 40° C. Preferably, the soy-based protein meal has been modified with a protease enzyme and the overall composition includes from about 20% to about 80% of soy-based protein meal based on the total dry weight of the composition. More preferably, the soy-based protein meal has been modified with a protease enzyme and the overall composition includes from about 50% to about 70% of soy-based protein meal based on the total dry weight of the composition.

In another aspect, a PFAS-free bio-based fire foam concentrate composition with a bio-based content of greater than 80% on a dry weight basis is disclosed, the composition comprising a soy protein flour or meal that has been enzymatically modified with a protease enzyme to a viscosity of less than 2000 cps utilizing spindle #4 at 100 rpm at 40° C., a mixture of CAPB and SLS surfactants, 1-biobutanol, and a citric acid builder.

In yet another aspect, a method of extinguishing a fire using a PFAS-free bio-based fire foam concentrate composition is disclosed, the method comprising providing a PFAS-free bio-based fire foam concentrate composition, comprising water, a plant protein, a bio-based surfactant, an alcohol, and a builder; mixing the PFAS-free bio-based fire foam concentrate composition with water to form a diluted wetting agent; and directing the diluted wetting agent to a fire to extinguish the fire. Preferably, the plant protein used is a plant protein consisting essentially of a soy-based protein. Preferably, the plant protein used has been chemically or enzymatically modified. More preferably, the plant protein used has been modified with a protease enzyme. In a preferred embodiment, the plant protein used is a protein comprising a soy-based protein and has been modified with a protease enzyme to a Brookfield viscosity of less than 2000 cps utilizing spindle #4 at 100 rpm at 40° C. Preferably, the plant protein used is a protein comprising a soy-based protein and has been modified with a protease enzyme, and the composition preferably includes from about 20% to about 80% of soy-based based on the total dry weight of the composition. More preferably, the composition used preferably includes from about 50% to about 70% of soy-based based on the total dry weight of the composition. In more preferred embodiments of the embodiments described above, the plant protein is a protein consisting essentially of a soy-based protein.

In another aspect, a method of extinguishing a fire using a PFAS-free bio-based fire foam concentrate composition is disclosed, the method comprising: providing a PFAS-free bio-based fire foam concentrate composition, comprising water, an extracted and flash desolventized soy-based protein flour, a bio-based surfactant, an alcohol, and a builder; mixing the PFAS-free bio-based fire foam concentrate composition with water to form a diluted wetting agent; directing the diluted wetting agent to a fire to extinguish the fire. Preferably, the soy-based protein flour used has been chemically or enzymatically modified. More preferably, the soy-based protein flour used has been modified with a protease enzyme. Preferably, the soy-based protein flour used has been modified with a protease enzyme to a Brookfield viscosity of less than 2000 cps utilizing spindle #4 at 100 rpm at 40° C. In a preferred embodiment, the soy-based protein flour used has been modified with a protease enzyme and the composition used includes from about 20% to about 80% of soy-based protein flour based on the total dry weight of the composition. More preferably, the composition used includes from about 50% to about 70% of soy-based protein flour based on the total dry weight of the composition.

In another aspect, a method of extinguishing a fire using a PFAS-free bio-based fire foam concentrate composition is disclosed, the method comprising: providing a PFAS-free bio-based fire foam concentrate composition, comprising: water, an extracted, and roasted soy-based protein meal, a bio-based surfactant, an alcohol, and a builder; mixing the PFAS-free bio-based fire foam concentrate composition with water to form a diluted wetting agent; and directing the diluted wetting agent to a fire to extinguish the fire. Preferably, the soy-based protein meal used has been chemically or enzymatically modified. More preferably, the soy-based protein meal used has been modified with a protease enzyme. In a preferred embodiment, the soy-based protein meal used has been modified with a protease enzyme to a Brookfield viscosity of less than 2000 cps utilizing spindle #4 at 100 rpm at 40° C. In a preferred embodiment, the soy-based protein meal used has been modified with a protease enzyme and the composition used includes from about 20% to about 80% of soy-based protein meal based on the total dry weight of the composition. More preferably, the composition used includes from about 50% to about 70% of soy-based protein meal based on the total dry weight of the composition.

In yet another aspect, a method of extinguishing a fire using a PFAS-free bio-based fire foam concentrate is disclosed, the method comprising: providing a PFAS-free bio-based fire foam concentrate composition with a bio-based content of greater than 80% on a dry weight basis, the composition comprising a soy protein flour or meal that has been enzymatically modified with a protease enzyme to a viscosity of less than 2000 cps utilizing spindle #4 at 100 rpm at 40° C., a mixture of CAPB and SLS surfactants, 1-biobutanol, and a citric acid builder; mixing the PFAS-free bio-based fire foam concentrate composition with water to form a diluted wetting agent; and directing the diluted wetting agent to a fire to extinguish the fire.

The summary provided herein is intended to provide examples of particular disclosed embodiments and is not intended to cover all potential embodiments or combinations of embodiments. Therefore, this summary is not intended to limit the scope of the invention disclosure in any way, a function which is reserved for the appended claims.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

FIG. 3 shows a second method of extinguishing a fire using a PFAS-free bio-based fire foam concentrate composition;

US 12,611,561 B2

5

Figure 1:
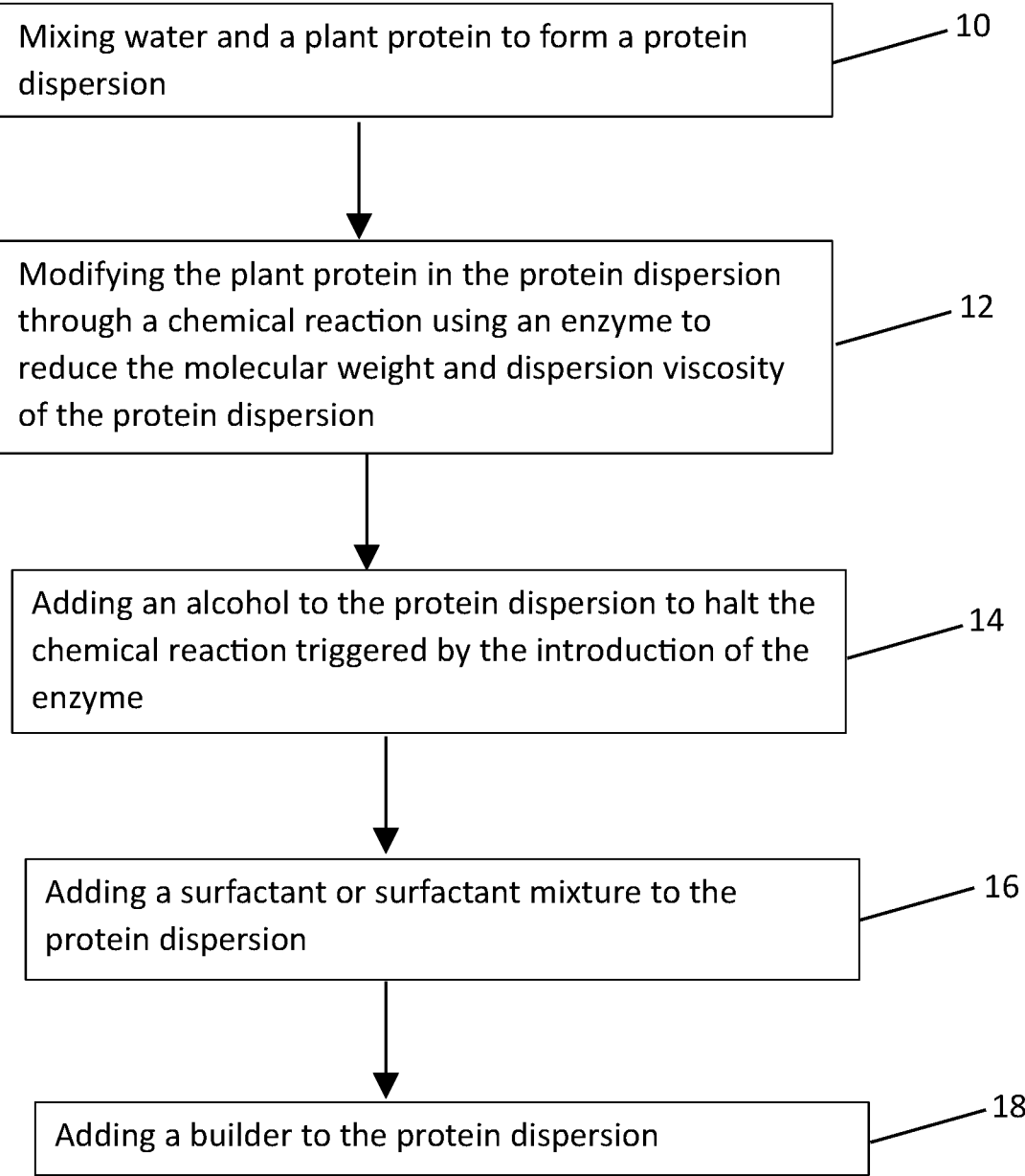
FIG. 1 shows a method for producing a PFAS-free fire foam concentrate.

FIG. 5 shows a fourth method of extinguishing a fire using a PFAS-free bio-based fire foam concentrate composition.

The figures are provided to illustrate concepts of the invention disclosure and are not intended to embody all potential embodiments of the invention. Therefore, the figures are not intended to limit the scope of the invention disclosure in any way, a function which is reserved for the appended claims.

DETAILED DESCRIPTION OF THE DISCLOSURE

The present disclosure is directed to PFAS-free fire foam concentrate compositions comprising water, plant proteins, surfactants, alcohols, and builders; methods for making such compositions; and methods for using such compositions. It is preferable that the PFAS-free fire foam concentrate compositions be derived from bio-based or naturally occurring components wherein the bio-based content of the present disclosed embodiments is greater than 80%.

The water of the present disclosed embodiments may be from any water source such as fresh water, ocean, or sea water.

The protein of the present disclosed embodiments can be any protein, preferably a plant protein. For example the protein of the disclosed embodiments can be sourced from soy, linseed, flaxseed, cottonseed, canola, sunflower, peanut, lupin, and mixtures thereof. Cereal grain sources such as wheat gluten, pea protein, and corn proteins can also be used. Most preferably however, the protein of the disclosed embodiments comprises a soy protein. Soy protein suitable for use in the inventive compositions is traditionally obtained by removing some or most of the oil from the soybean yielding a residual soy flake that is ground into fine soy protein flour generally containing from 50-55% soy protein with remaining material comprising various low molecular weight carbohydrates, hemi-cellulosics, and ash. For the purposes of this embodiment, the term "soy protein" includes these other impurities. Hexane or some other organic extractant is used to extract the majority of the non-polar oils from the soybeans. Generally the extraction is carried out on the crushed soybeans. Extrusion and extraction methods known to one of ordinary skill in the art of soybean oil processing may also be utilized to reduce the oil content of the crushed soy flake. After extraction, the oil level in the crushed soy flake typically is less than 5 percent by weight, preferably less than 3 percent by weight, more preferably less than 2 percent by weight, and most preferably less than 1 percent by weight of the soy protein flake. Desolventization, that is removal of the residual extraction solvent from the soy protein flake, may be accomplished via a low temperature flash desolventizing process or be a traditional high temperature roasting process.

In one embodiment of the present invention, the extracted, and flash desolventized, soy protein flake is converted to a flour by grinding to a mesh screen size of from about 100 mesh to about 600 mesh. More preferably, the extracted, and flash desolventized, soy protein flake has been ground to a mesh screen size of from about 200 mesh to about 400 mesh. Most preferably the extracted, and flash desolventized, soy protein flake has been ground to a mesh screen size of from about 200 mesh to about 325 mesh.

The chemical and physical properties of the soy protein can vary based on the thermal history of the oilseed flake or flour. One measurement that may be used to help assess the degree of heat impact or extent of heating of a protein within the flake or flour is the Protein Dispersability Index (PDI). The PDI is a measurement of the degree the extracted and desolventized flake or flour may be dispersed in water without particle settling. The PDI is generally determined by measuring the percentage of nitrogen in a sample that may be dispersed in water under standardized conditions, according to the AOCS Ba10a-05.

The PDI is often used to specify the extracted and desolventized flake or flour. For instance, typical soy protein flakes prepared with no added heating (untoasted) will have a PDI value greater than 95, and the proteins in the flake can be characterized as native, as in not denatured, where denaturation refers to the process by which the natural configuration and conformation of the protein is lost due to chemical (acids, bases, chaotropic agents, hydrolases, etc.) or physical (heat, shear, etc.) processes. The properties of the soy protein flake or flour may also be shown to be dependent on the extent of native and denatured protein present. As such, the PDI may be used as an indicator of certain chemical and physical properties of the soy protein flake or flour. Examples of such properties for soy protein flake or flour include protein solubility at neutral pH, viscosity, color, and extent of lysine modification. Hence, a soy protein flake or flour with an intensive thermal history and PDI of 20, typically forms a more viscous dispersion than a soy protein flake or flour having little (PDI of 70) to no (PDI of 90) thermal history.

Three grades of commonly available soy flake or flour are 90 PDI (untoasted), 70 PDI (lightly toasted) and 20 PDI (heavily toasted), but one skilled in the art would recognized that many intermediate grades could be prepared, and that even more extensive heating would result in flakes or flours with a lower PDI value. Commercial sales of ground soy protein flour are often expressed in terms of a Ground Mesh Size and in the case of soy protein flour, a PDI value. For example, a 100/90 product is a ground soy protein flour that passes through a 100 mesh screen and has a Protein Dispersibility Index of 90%. A 200/20 soy protein flour on the other hand indicates the flour passes through a 200 mesh screen, but has only a 20% PDI.

In one embodiment of the present invention, the extracted and desolventized soy protein flake or flour has a PDI value of from about 20 to about 90. More preferably, the soy protein flake or flour has a PDI value of from about 70 to 90. Most preferably, the soy protein flake or flour has a PDI value of greater than 80 PDI.

Further in the embodiment, the extracted and desolventized soy protein flake or flour comprises from about 1% to 99% dry weight of the fire foam composition. More preferably, the soy protein flake or flour comprises from about 20% to 80% of the composition. Most preferably, the soy protein flake or flour comprises from about 50% to 70% of the composition.

The vast majority of solvent extracted soybean however, is produced under high heat conditions for solvent removal and thereby is substantially heat denatured (less than 25 PDI) to produce a product called soy protein meal. Soy protein meal is useful in various animal feed products for example and generally contains 46-49% protein.

In one embodiment of the present invention, the soy protein meal is utilized as the protein source in the composition. The soy protein meal having a PDI value of less than 25, has been ground to a mesh screen size of from about 100 mesh to about 600 mesh. More preferably, the soy protein meal has been ground to a mesh screen size of from about 200 mesh to about 400 mesh. Most preferably the soy protein meal has been ground to a mesh screen size of from about 200 mesh to about 325 mesh.

In another embodiment of the present invention, the soy protein meal comprises from about 1% to 99% of the fire foam concentrate composition on a dry weight basis. More preferably, the soy protein meal comprises from about 20% to 80% of the composition on a dry weight basis. Most preferably, the soy protein meal comprises from about 50% to 70% of the composition on a dry weight basis.

The plant protein of the present disclosed embodiments may be modified in order to change its molecular weight or chemical functionality. Enzyme conversion of the plant protein is a particularly useful modification as there are many different types of enzymes available. For example, a plant protein may be modified with a protease enzyme to reduce the molecular weight of the protein, thereby reducing the viscosity of the water dispersed plant protein. This modification is necessary in order to incorporate plant proteins into the fire foam concentrate formulation while maintaining a useful overall viscosity of the concentrate. Other enzyme modifications may also be used such as utilizing a phosphorylase enzyme to impart phosphate functionality on the protein, or utilizing a carboxylate enzyme to impart additional carboxyl functionality on the protein. Additionally, an oxidase or reductase enzyme may be utilized to change the functionality of the protein. Combinations of these enzyme modifications may also be used to impart additional functionality on the protein.

In a particularly useful embodiment, the plant protein is a soy flour ground to a mesh size of 200 with a PDI value of 90 (200/90, multiple sources). A 30% dispersion of the soy flour is prepared by slowly mixing in the dry soy flour to rapidly stirring water containing 0.1% to 1% of sodium bisulfite or sodium sulfite. The sulfite percentage is based on the commercial dry weight of the soy flour. As the dry soy flour is dispersed into the stirring water/sulfite solution, the viscosity of the dispersion increases dramatically to greater than 100,000 cps. Over time, the sulfite reacts with specific linkages within the protein thereby reducing the viscosity of the dispersion marginally. However, the viscosity at this point is still too high to be useful as a component of the fire foam concentrate. A protease enzyme is utilized to reduce the molecular weight of the protein and thereby reducing the viscosity of the soy protein dispersion. Specifically, an alcalase enzyme (Alcalase, Novozyme) is used to reduce the molecular weight of the soy protein. The alcalase enzyme is added at a concentration sufficient to substantially reduce the viscosity of the soy flour dispersion, typically, below 1,000 cps after a reaction time of 1-2 hours at 30-40° C. and a dispersion pH of 7-8. At this point, the soy flour dispersion with a reduced viscosity is ready to be incorporated into the fire foam concentrate formulation.

In another embodiment, the plant protein is a soy meal ground to a mesh size of 200 with a PDI value of less than 25 (multiple sources). A 30% dispersion of the soy meal is prepared by slowly mixing in the dry soy meal to rapidly stirring water containing 0.1% to 1% of sodium bisulfite or sodium sulfite. The sulfite percentage is based on the commercial dry weight of the soy meal. As the dry soy meal is dispersed into the stirring water/sulfite solution, the viscosity of the dispersion increases dramatically to greater than 100,000 cps. Over time, the sulfite reacts with specific linkages within the protein thereby reducing the viscosity of the dispersion marginally. However, the viscosity at this point is still too high to be useful as a component of the fire foam concentrate. A protease enzyme is utilized to reduce the molecular weight of the protein and thereby reducing the viscosity of the soy protein meal dispersion. Specifically, an alcalase enzyme (Alcalase, Novozyme) is used to reduce the molecular weight of the soy protein meal. The alcalase enzyme is added at a concentration sufficient to substantially reduce the viscosity of the soy protein meal dispersion, typically, below 2,000 cps after a reaction time of 1-2 hours at 30-40° C. and a dispersion pH of 7-8. At this point, the soy protein meal dispersion with a reduced viscosity is ready to be incorporated into the fire foam concentrate formulation.

The surfactant of the present disclosed embodiments is preferably a plant oil derived surfactant. The plant oil may be sourced from soy, linseed, flaxseed, cottonseed, canola, sunflower, peanut, lupin, palm kernel, cocoanut, and mixtures thereof. Plant oils are generally chemically modified to convert the oil esters into various alkyl and alkenyl carboxylate salts in order to provide useful surfactant properties. It is generally accepted that the $C_8$ to $C_{14}$ carbon carboxylate salts have preferred surfactant ability. The alkyl and alkenyl carboxylate salts may be further modified to improve their surfactant ability. These modified surfactants may be divided into three general categories, cationic, anionic, and non-ionic surfactants. For example, $C_{12}$ lauryl carboxylate may be chemically modified to lauryl alcohol which may then be sulfate modified to the anionic sodium lauryl sulfate (SLS) or chemically ethoxylated and sulfated to sodium lauryleth sulfate (SLES). Similarly, the reaction of dimethylaminopropylamine (DMAPA) with fatty acids from coconut or palm kernel produces a useful surfactant, cocamidopropyl betaine (CAPB). Alkyl and alkenyl carboxylate salts may also be modified to produce glucoside containing moieties. For example, $C_{10}$ capryl carboxylate may be chemically modified to capryl alcohol which may then be reacted with glucose to form non-ionic capryl glucoside which has a very high bio-based content.

In one embodiment of the present invention, the fire foam concentrate comprises a chemically modified plant oil based surfactant chosen from a list comprising a cationic surfactant, an anionic surfactant, a non-ionic surfactant, and mixtures thereof.

Further in the embodiment, the chemically modified plant oil based surfactant on a dry weight basis comprises of from about, 5% to about 50% of the fire foam concentrate composition. More preferably, the chemically modified plant oil based surfactant on a dry weight basis comprises from about 7% to about 30% of the fire foam concentrate composition. Most preferably, the chemically modified plant oil based surfactant on a dry weight basis comprises from about 8% to about 20% of the fire foam concentrate composition.

In a particularly useful embodiment, the modified plant oil based surfactant is a mixture of CAPB and SLS comprising on a dry basis of from about 8% to about 15% of the fire foam concentrate composition.

In another useful embodiment, the modified plant oil is a nonionic surfactant such as capryl glucoside comprising on a dry basis of from about 8% to about 15% of the fire foam concentrate composition. The nonionic surfactants may be useful where ocean or sea water is used to dilute the fire foam concentrate for application onto a fire.

The alcohol of the present disclosed embodiments is preferably an alkyl mono-alcohol. The alcohol provides many uses in the formulation. In the concentrate formulation the alcohol acts as an anti-foaming agent to prevent undo foam generation as the concentrate is prepared. Most importantly, in the concentrate formulation the alcohol prevents degradation from microbial contamination of the modified soy protein. This is critical for the long term storage stability of the soy-based concentrate. Many commercial antimicrobials are oxidative or reductive in their mechanism of action.

Once reacted, they are no longer effective as antimicrobial agents and have to be replenished. Short carbon chain alcohols on the other hand, disrupt the cell wall of the microbes as the mechanism of action and are not depleted. In the diluted fire foam application, the alcohol enhances the generation of micro- and nano-bubbles which increases the viscosity of the foam structure. The alcohol of the present disclosed embodiments is chosen from the group containing $C_1$-$C_5$ carbon alcohols such as methanol, ethanol, propanol, butanol, and pentanol. Various OH isomers of the $C_3$-$C_5$ alcohols may be utilized. In one particularly useful embodiment, the chosen alcohol is 1-butanol preferably, 1-biobutanol.

Further in the embodiment, the alkyl mono-alcohol comprises of from about 1% to about 20% of the fire foam concentrate composition on a dry weight basis. More preferably, the alkyl mono-alcohol comprises of from about 5% to about 15% of the dry weight fire foam concentrate composition. Most preferably, the alkyl mono-alcohol comprises of from about 5% to about 10% of the dry weight fire foam concentrate composition.

The builder of the present disclosed embodiments may be any commonly used builder or co-builder used in various soap and detergent formulations such as phosphates, zeolites and carboxylated organic compounds. These builders and co-builders are useful in reducing the water hardness by reacting with multi-valent metal ions such as Calcium, Magnesium, and Iron, for instance. This is especially important where ocean or sea water is used to dilute the fire foam concentrate as ocean and sea water has extremely high water hardness. These multi-valent metal ions are harmful to the generation of foam in the fire foam application so the builder/co-builder helps to facilitate foam generation. In a particularly useful embodiment, citric acid is used as a builder due to its propensity to coordinate with multi-valent metal ions and also for its bio-based sourcing.

Further in the embodiment, the builder/co-builder comprises of from about 0.1% to about 5% of the fire foam concentrate formulation on a dry weight basis. More preferably, the builder/co-builder comprises of from about 0.2% to about 2% of the dry weight fire foam concentrate formulation. Most preferably, the builder/co-builder comprises of from about 0.2% to about 1% of the dry weight fire foam concentrate formulation.

In a typical process for producing the PFAS-free fire foam concentrate comprising water, a plant protein, a surfactant, an alcohol, and a builder, a 30% dispersion of the plant protein is modified with a protease enzyme to reduce the molecular weight of the protein and consequently, the dispersion viscosity. The viscosity of the protein dispersion is reduced to less than 2000 cps at 40° C., utilizing a Brookfield viscometer (RV DVII+, spindle #4, 100 rpm. The reaction is halted by adding an alcohol. The alcohol has the effect of an antifoam on the dispersion and the viscosity is further reduced. The protein dispersion is combined with the surfactant mixture, followed by the builder and mixed to a uniform dispersion. The viscosity of the completed fire foam concentrate at this point is between 100-300 cps (at 25° C.). With reference to FIG. 1, a process for producing a PFAS-free fire foam concentrate includes (10) mixing water and a plant protein to form a protein dispersion, (12) modifying the plant protein in the protein dispersion through a chemical reaction using an enzyme to reduce the molecular weight and dispersion viscosity of the protein dispersion, (14) adding an alcohol to the protein dispersion to halt the chemical reaction triggered by the introduction of the enzyme, (16) adding a surfactant or surfactant mixture to the protein dispersion, (18) adding a builder to the protein dispersion.

The soy-based fire foam concentrates of the present disclosed embodiments, are useful in the suppression of Class A and Class B fire suppression, as well as training foams for training firefighting personnel on the use of fire foam concentrates. Typically, the fire foam concentrates will be diluted to about 0.1% to about 6% concentration with either fresh water, ocean water, or sea water for use in fire suppression.

The following examples are presented to illustrate the present disclosure and to assist one of ordinary skill in making and using the same. The examples are not intended in any way to otherwise limit the scope of the disclosure.

EXAMPLES

The following are examples of synthesis and test procedures utilized in preparing fire foam concentrate compositions and evaluating the properties of the fire foam concentrate compositions.

Example 1—Preparation of a Soy-Based Fire Foam Concentrate

A 30 g soy flour dispersion was prepared by adding 10 g of 200/90 soy flour (multiple sources) to a sealable container along with 0.1 g of sodium sulfite and 20 g of tap water heated to 40° C. This was hand stirred to a uniform dispersion. 10 drops of Alcalase enzyme (Novozyme) was added and mixed. The container was sealed, set in a water bath at 50° C. and allowed to react for 120 minutes. The dispersion became somewhat foamy as it had incorporated air or carbon dioxide due to the action of the enzyme. To this mixture was added 3 g of n-butanol which acted as an antifoam and reduced the viscosity of the dispersion tremendously. To another container a stock solution of a mixture of cocamidopropyl betaine (CAPB) and sodium dodecyl sulfate (SDS) was prepared by adding 15 g of SDS to a 530 g solution of CAPB (estimated to be 30% solids). Gentle mixing was required to obtain a clear soap solution. This increased the soap concentration to approximated 32% solids. To the soy flour dispersion containing n-butanol was added 15 g of the 32% CAPB/SDS mixture along with 0.2 g of dry citric acid. This was mixed together until the citric acid was fully dissolved. The resultant mixture was very fluid. For the next six months the prepared fire foam concentrate was evaluated for microbiological activity by observing any pressure buildup in the sealed vessel, and also performing an olfactory sniff test. There was no evidence of microbiological activity even after six months, indicating that the n-butanol was performing the function of an effective antimicrobial reagent.

Example 2—Laboratory Foam Evaluation of Soy-Based Fire Foam Concentrate

The foam concentrate composition prepared in Example 1 was evaluated for foaming properties by adding 2 g of the foam concentrate of Example 1 to 198 g of room temperature tap water in an 900 ml stainless steel Hamilton Beach mixing beaker. The Hamilton Beach mixer was set to speed setting 1, and the beaker was attached to the mixer and mixing begun. A stop watch measured the time it took for the generated foam to reach to full capacity of the 800 ml beaker (4× volume). This was measured to be 13 seconds. Typically, a commercial foam concentrate product achieves the 800 ml foam test in 10-15 seconds. The diluted 1% foam from Example 1 produced a high viscosity foam that was persistent for several hours.

Example 3—Laboratory Evaluation of Diluted Soy-Based Fire Foam Concentrate for Wetting Ability The soy-based fire foam concentrate from Example 1 was diluted to 0.2% with normal tap water and placed in a plastic vessel capable of delivering a uniform droplet size. Similarly, a commercial PFAS containing fire foam concentrate (Phoscheck) was diluted to the same 0.2% with normal tap water and placed in a plastic vessel capable of delivering a uniform droplet size. Tap water was used as the control in the evaluation and also placed in a plastic vessel capable of delivering a uniform droplet size. Strips of pine board measuring 2 inches by 1 inch and ⅛ inch thickness, was sanded with 400 grit sandpaper to a smooth finish. Three drops of the water or test liquids were added to the pine boards and a timer was started. The time was recorded from when the droplet was placed on the board, to the time where the droplet was completely soaked into the board. The average time of the three drops was recorded to the nearest 15 seconds, with the following results.

TABLE 1

| Sample | Tap Water | Diluted PFAS | Diluted Example 1 |
|---|---|---|---|
| Time | 14 min 45 secs | 2 min 15 secs | 3 min |

From the results above, it is determined that the formulation of Example 1 substantially reduced the absorption time (wetting ability) into pine wood thereby demonstrating its applicability as a Class A wetting agent.

Example 4—Preparation of Pilot Scale Soy-Based Fire Foam Concentrate

Vessel #1
In a 5-gal vessel with stirring, a concentrated soap solution was prepared by charging Vessel #1 with 5,300 g of cocamidopropyl betaine (CAPB) solution (32% solids). This was heated to 30° C. with gentle stirring. To the stirring solution was added 150 g of dry sodium dodecyl sulfate (SDS) and stirred until the dry SDS was completely dissolved.
Vessel #2
A soy flour dispersion was prepared in a 5-gallon vessel capable of rapid stirring by adding 7,570 g of 40° C. tap water along with 50 g of sodium sulfite. To the rapidly stirring water solution 3,485 g of a 200/90 soy flour was added in multiple portions. Due to the high viscosity of the soy flour dispersion 100 ml of the Alcalase enzyme was added in multiple portions to allow the mixer to perform its function. The addition of the soy flour was stopped at 3,485 g addition due to the high viscosity. The dispersion was adjusted to pH 7-8 by adding small amounts of a 2:1 dry mix of Sodium Carbonate/Sodium Bi-carbonate until a pH of 7.2 was obtained (25 g). An additional 100 ml of the Alcalase enzyme was added and allowed to react. A viscosity check of the dispersion was performed after 1 hour of reaction with the Alcalase enzyme and measured to be 1450 cps (RV DVII+, spindle #4, 100 rpm). After 1.5 hours, the viscosity of the dispersion was measured to be 1375 cps, and after 2.0 hours the viscosity was measured to be 1330 cps. At this point the heat was removed and 1000 g of n-butanol was added which reduced the viscosity of the dispersion. The contents of Vessel #1 was then added to the Vessel #2 containing the enzyme reacted soy flour mixture, along with 75 g of dry citric acid and the mixture stirred until the citric acid was completely dissolved. A Brookfield viscosity was performed on the resultant foam concentrate (RV II+, spindle #4, 100 rpm) and measured to be 175 cps at 25° C.

Example 5—Preparation of Pilot Scale Soy-Based Fire Foam Concentrate

A second foam concentrate sample was prepared as in Example 4, by adding the Alcalase enzyme in one portion to the soy flour dispersion.
Vessel #1
In a vessel with stirring, a concentrated soap solution was prepared by charging Vessel #1 with 5,300 g of cocamidopropyl betaine (CAPB) solution. This was heated to 30° C. with gentle stirring. To the stirring solution was added 150 g of dry sodium dodecyl sulfate (SDS) and stirred until the dry SDS was completely dissolved.
Vessel #2
A soy flour dispersion was prepared in a 5-gallon vessel capable of rapid stirring by adding 7,570 g of 40° C. tap water along with 50 g of sodium sulfite. To the rapidly stirring water solution 3,485 g of a 200/90 soy flour was added in multiple portions. Rapid stirring was required to generate a uniform dispersion. The dispersion was adjusted to pH 7-8 by adding small amounts of a 2:1 dry mix of Sodium Carbonate/Sodium Bi-carbonate until the desired pH was obtained. 200 ml of Alcalase enzyme (Novozyme) was then added slowly in one portion and the mixture was heated to 50° C. A viscosity check of the dispersion was performed after 1 hour of reaction with the Alcalase enzyme and measured to be 1170 cps (RV II+, spindle #4, 100 rpm). After 1.5 hours, the viscosity of the dispersion was measured to be 1000 cps, and after 2.0 hours the viscosity was measured to be 980 cps. At this point the heat was removed and 1000 g of n-butanol was added which reduced the viscosity of the dispersion. The contents of Vessel #1 was added to the Vessel #2 reacted soy flour mixture along with 75 g of dry citric acid and the mixture stirred until the citric acid was completely dissolved. A Brookfield viscosity was performed on the resultant foam concentrate (RV II+, spindle #4, 100 rpm) and measured to be 162 cps at 25° C. The percent dry solids was measured on a Mettler Moisture Meter and found to be 30.5% solids.

Example 6—Large Scale Evaluation of Soy-Based Fire Foam Concentrate

The Dalton city fire department (Dalton, GA) was commissioned to test the fire foam concentrates prepared in Examples 4 and 5 for applicability as training foam and as a Class A fire foam.
Foamability Test
Procedure
A 200 ft×2 inch standard fire hose, along with a standard proportion inductor with the water pressure set at 100 psi and 100 gpm, was used to mix and spray a diluted wetting agent in the form of a fire foam. The Inductor was proportioned at 1%, 3%, and 6% of the Example 4 fire foam concentrate to produce the diluted fire foam.

Results

All proportioned levels of the fire foam concentrate of Example 4 produced an adequate foam blanket. It was noted that the higher the proportioned level of concentrate, the higher the foam density.

Pallet Test

Procedure

A stack of 2 standard wood pallets was lit with a propane torch and allowed to burn for 5 minutes until the entire pallet was consumed with flame. A 200 ft×2 inch standard fire hose, along with a standard proportion inductor with the water pressure set at 100 psi and 100 gpm, was used to mix and spray the diluted wetting agent.

The inductor was proportioned at 1% of the Example 4 fire foam concentrate and sprayed onto the burning wood pallets.

Results

The 1% proportioned of the Example 4 fire foam concentrate immediately put out the pallet fire. After 2 hours the pallet was attempted to be reignited to measure the effectiveness of the wetting agent but was unsuccessful. The Example 4 fire foam concentrate thereby passed the re-ignition test.

Example 7—Preparation of Pilot Scale Soy-Based Fire Foam Concentrate Utilizing Soy Protein Meal A third foam concentrate sample was prepared as in Examples 4 and 5, utilizing soy protein meal as the soy protein base.

Vessel #1

In a vessel with stirring, a concentrated soap solution was prepared by charging Vessel #1 with 5,300 g of cocamidopropyl betaine (CAPB) solution. This was heated to 30° C. with gentle stirring. To the stirring solution was added 150 g of dry sodium dodecyl sulfate (SDS) and stirred until the dry SDS was completely dissolved.

Vessel #2

A soy meal dispersion was prepared in a 5-gallon vessel capable of rapid stirring by adding 7,570 g of 40° C. tap water along with 50 g of sodium sulfite. To the rapidly stirring water solution 3,485 g of 200 mesh soy meal was added in multiple portions. Rapid stirring was required to generate a uniform dispersion. The dispersion was adjusted to pH 7-8 by adding small amounts of a 2:1 dry mix of Sodium Carbonate/Sodium Bi-carbonate until the desired pH was obtained. 200 ml of Alcalase enzyme (Novozyme) was then added slowly in one portion and the mixture was heated to 50° C. A viscosity check of the dispersion was performed after 1 hour of reaction with the Alcalase enzyme and measured to be 1500 cps (RV II+, spindle #4, 100 rpm). After 1.5 hours, the viscosity of the dispersion was measured to be 1250 cps, and after 2.0 hours the viscosity was measured to be 1,100 cps. At this point the heat was removed and 1000 g of n-butanol was added which reduced the viscosity of the dispersion. The contents of Vessel #1 was added to the Vessel #2 reacted soy meal mixture along with 75 g of dry citric acid and the mixture stirred until the citric acid was completely dissolved. A Brookfield viscosity was performed on the resultant foam concentrate (RV II+, spindle #4, 100 rpm) and measured to be 190 cps at 25° C. The percent dry solids was measured on a Mettler Moisture Meter and found to be 30.5% solids.

Example 8—NFPA Evaluation of Example 4 in Class A Fire Foams

Fire Foam Concentrate from Example 4 was evaluated at the Chippewa Valley Technical College in Eau Claire, WI, as a Class A wetting agent using protocols contained within the National Fire Protection Association (NFPA) 18: Standard on Wetting Agents (2017 edition). Four tests associated with extinguishment of Class A fires were performed:
1. Wood crib fire test
2. Deep-seated fire test
3. Wood fiberboard penetration
4. 50 square foot heptane fire test The first of the Class A fire tests in NFPA 18 Chapter 8 tests the ability of a wetting agent solution to extinguish wood crib fires with the solution prepared at the minimum concentration specified for use (0.3% in this case). Tests are conducted according to the procedures detailed in this section and ANSI/UL 711 CAN/ULC S508 for Class A fires utilizing a 3-A wood crib. The solution is applied with a nominal 9.5 L (2.5 gal) listed 2-A rated water extinguisher. As per UL 711, two consecutive crib extinguishments are required, and the steps listed below are performed for each of the trials.

Wood Crib Fire Test
1. Crib is constructed of 18 layers of 8 wood members each 38 mm by 38 mm by 735 mm
2. Members are constructed of kiln dried spruce or fir having a moisture content of 9 to 15 percent.
3. Crib is placed on an angle iron frame above a burn pan.
4. The net mass of the crib is determined prior to commencing the test.
5. Ignition of the crib is accomplished by burning 2.8 liters of heptane in the pan.
6. The crib fire is extinguished with the wetting solution when its mass had been reduced to 55±1 percent of its original mass.
7. Discharge is to be continuous until the extinguisher is completely discharged.
8. After 15 minutes, the crib is examined for any hot spots or re-ignition.

Results of the Crib Fire Test

Key data associated with the wood crib fire tests are contained in Table 2 and Table 3. The 0.3% solution of TF 1122 wetting agent successfully extinguished two 3-A cribs and no re-ignition or hot spots were found after the 15 minute waiting periods. The consecutive extinguishment of two cribs with the 9.5 L extinguisher filled with the wetting agent solution constitutes a passing test.

TABLE 2

| Crib #1 Example 4 Concentrate @0.3% | | | |
|---|---|---|---|
| Starting Weight: | 156.5 lbs | Ignition Time (min:secs): | 0:00 |
| Hit Weight: | 86.0 lbs (55% of original) | Heptane Consumed: | 3:02 |
| % moisture Top | 13.0 | Start of Extinguishment: | 7:19 |
| Side 1 | 12.1 | End of Extinguishment: | 8.32 |

TABLE 2-continued

| Crib #1 Example 4 Concentrate @0.3% | | | |
|---|---|---|---|
| Side 2 | 11.5 | Duration of Extinguishment: | 1:11 |
| Side 3 | 11.2 | End of waiting period: | 23:32 |
| Side 4 | 11.5 | Result: | Full Extinguishment |
| Average | 11.86 | | |
| | (Criteria is between 9% and 15%) | | |

TABLE 3

| Crib #2 Example 4 Concentrate @0.3% | | | |
|---|---|---|---|
| Starting Weight: | 163.5 lbs | Ignition Time (min:secs): | 0:00 |
| Hit Weight: | 90.0 lbs (55% of original) | Heptane Consumed: | 3:06 |
| % moisture Top | 14.7 | Start of Extinguishment: | 7:41 |
| Side 1 | 15.5 | End of Extinguishment: | 8:52 |
| Side 2 | 14.1 | Duration of Extinguishment: | 1:11 |
| Side 3 | 15.0 | End of waiting period: | 23:52 |
| Side 4 | 14.3 | Result: | Full Extinguishment |
| Average | 14.72 (Criteria is between 9% and 15%) | | |

Deep Seated Fire Test

The second of the Class A fire tests in NFPA 18 Chapter 8 tests whether the wetting agent solution can extinguish deep-seated cotton fires and exhibit less runoff than water. Tests were conducted three times with plain water and three times with the wetting agent solution prepared at three different concentrations. This test was performed two times on two different days. The first set of tests was performed with 1.0% solution and the second set was performed with both 0.1% and 0.3% solutions. The tests were conducted using a cylindrical basket of perforated sheet steel, 114 mm (4.5 in.) in diameter and 178 mm (7 in.) height, and ginned cotton weighing 100 g (3.5 oz). The steps listed below were performed for each of the six trials.

1. Stuff 50 g (1.75 oz) of cotton into the bottom half of the basket.
2. Heat a steel rod 35 mm (1.38 in.) in diameter and 33 mm (1.3 in.) long to 593° C. (1100° F.).
3. Place the rod on the cotton in the basket.
4. Immediately insert 50 g (1.75 oz) of cotton into the basket on top of the rod.
5. Pour 250 mL (8.5 fl oz) of test liquid (water or wetting agent solution) onto the cotton and catch the runoff in a pan placed below the basket.
6. Measure and record the volume of runoff.

Results of the Deep Seated Fire Test

Results of the 2 days of deep-seated fire trials are detailed in Table 4 and Table 5. The passing criteria of this test (extinguish the fire and exhibit less runoff than water) were surpassed with the all three concentrations (0.1%, 0.3%, and 1.0% solutions) of Example 4 Class A wetting agent. The cotton fire was extinguished in each of the trials with wetting agent solution, and the mean runoff of each test solution was less when compared with plain water. Not unexpectedly, the decrease in runoff volume was more pronounced with the higher concentrations. It was also noted more complete extinguishment of the cotton in each of the tests with wetting agent solution, while some hot spots remained after several of the water-only tests.

TABLE 4

| | | Day 1 Testing | | | |
|---|---|---|---|---|---|
| Test ID# | Extinguishing Solution Used | Volume of Solution Used (ml) | Volume of Runoff (ml) | Mean Runoff Volume (ml) | St. Dev. |
| W1 | Water | 250.0 | 188.2 | 168.2 | 56.75 |
| W2 | Water | 250.0 | 212.3 | | |
| W3 | Water | 250.0 | 104.2 | | |
| S1 | 1.0% Ex. 4 | 250.0 | 10.0 | 27.0 | 15.22 |
| S2 | 1.0% Ex. 4 | 250.0 | 31.8 | | |
| S3 | 1.0% Ex. 4 | 250.0 | 39.3 | | |

TABLE 5

| | | Day 2 Testing | | | |
|---|---|---|---|---|---|
| Test ID# | Extinguishing Solution Used | Volume of Solution Used (ml) | Volume of Runoff (ml) | Mean Runoff Volume (ml) | St. Dev. |
| W1 | Water | 250.0 | 181.2 | 168.2 | 56.75 |
| W2 | Water | 250.0 | 161.5 | | |
| W3 | Water | 250.0 | 120.2 | | |
| S1 | 0.1% Ex. 4 | 250.0 | 97.8 | 27.0 | 15.22 |
| S2 | 0.1% Ex. 4 | 250.0 | 75.7 | | |
| S3 | 0.1% Ex. 4 | 250.0 | 152.6 | | |
| S4 | 0.3% Ex. 4 | 250.0 | 95.3 | 107.6 | 52.44 |
| S5 | 0.3% Ex. 4 | 250.0 | 62.4 | | |
| S6 | 0.3% Ex. 4 | 250.0 | 165.1 | | |

Wood Fiberboard Penetration Test

The third of the Class A fire test in NFPA 18 Chapter 8 tests the wetting agent solution's ability to extinguish wood fiberboard fires and exhibit less runoff and weight loss than water. Tests were conducted three times with plain water and three times with the wetting agent solution prepared at three concentrations. This test was performed two times on two different days. The first set of tests was performed with 1.0% solution and the second set was performed with both 0.1% and 0.3% solutions.

The tests were conducted with fiber insulation board squares measuring 305 mm×305 mm×13 mm (12 in.×12 in.×½ in.) and were performed by following the steps listed below.

1. Weigh the test board and place it on a wire grid.

2. Expose the test board to an alcohol flame from a burning pan that is placed immediately below the test board for 105 seconds.

3. Remove the fuel pan and place a clean, dry pan under the test board to collect the water or agent runoff.

4. Spray 250 mL (8.5 fl oz) of test liquid (water or wetting agent solution) on the upper surface of the test board using a small sprinkler bottle.

5. Measure and record the volume of runoff.

6. Dry and weigh the boards and calculate the weight loss.

Results of the Fiberboard Penetration Test

Results of the two days of wood fiberboard fire test trials are detailed in Table 6 and Table 7. The passing criteria of this test (extinguish the fire, exhibit less runoff than water, and exhibit less weight loss than boards extinguished with water) were met with the all three concentrations (0.1%, 0.3%, and 1.0% solutions) of Example 5 Class A wetting agent. The test boards were extinguished in each of the three trials with wetting agent solution, and the mean runoff was less than the volume when compared with plain water. The reduction in mean runoff was small with 0.1 percent solution, but more pronounced with the higher concentrations.

TABLE 6

| | | Day 1 Testing | | | |
|---|---|---|---|---|---|
| Test ID# | Extinguishing Solution Used | Volume of Solution Used (ml) | Volume of Runoff (ml) | Mean Runoff Volume (ml) | St. Dev. |
| W1 | Water | 250.0 | 104.5 | 115.6 | 9.62 |
| W2 | Water | 250.0 | 121.4 | | |
| W3 | Water | 250.0 | 120.9 | | |
| S1 | 1.0% Ex. 4 | 250.0 | 8.5 | 11.1 | 7.26 |
| S2 | 1.0% Ex. 4 | 250.0 | 19.3 | | |
| S3 | 1.0% Ex. 4 | 250.0 | 5.5 | | |

TABLE 7

| | | Day 2 Testing | | | |
|---|---|---|---|---|---|
| Test ID# | Extinguishing Solution Used | Volume of Solution Used (ml) | Volume of Runoff (ml) | Mean Runoff Volume (ml) | St. Dev. |
| W1 | Water | 250.0 | 134.9 | 137.0 | 2.10 |
| W2 | Water | 250.0 | 139.1 | | |
| W3 | Water | 250.0 | 137.1 | | |
| S1 | 0.1% Ex. 4 | 250.0 | 131.0 | 130.1 | 0.85 |
| S2 | 0.1% Ex. 4 | 250.0 | 130.0 | | |
| S3 | 0.1% Ex. 4 | 250.0 | 129.3 | | |
| S4 | 0.3% Ex. 4 | 250.0 | 119.4 | 115.6 | 4.40 |
| S5 | 0.3% Ex. 4 | 250.0 | 110.8 | | |
| S6 | 0.3% Ex. 4 | 250.0 | 116.7 | | |

The fiberboard panels were then dried at room temperature for 24 hours as specified in NFPA 18 protocol and the results are summarized in Table 8 and 9.

TABLE 8

| | | Day 1 Testing | | | | | |
|---|---|---|---|---|---|---|---|
| Test Board | Extinguishing Solution Used | Panel Starting Weight | Panel Ending Weight | Weight Loss (g) | Percent Weight Loss | Mean Weight Loss (%) | St. Dev. |
| W1 | Water | 332.1 | 264.0 | 68.1 | 20.5 | 23.42 | 0.025 |
| W2 | Water | 335.0 | 251.2 | 83.8 | 25.0 | | |
| W3 | Water | 334.0 | 251.4 | 82.6 | 24.7 | | |
| S1 | 1.0% Ex. 4 | 330.5 | 261.2 | 69.3 | 21.0 | 20.58 | 0.014 |
| S2 | 1.0% Ex. 4 | 332.7 | 269.5 | 63.2 | 19.0 | | |
| S3 | 1.0% Ex. 4 | 333.1 | 260.6 | 72.5 | 21.8 | | |

TABLE 9

| | | Day 2 Testing | | | | | |
|---|---|---|---|---|---|---|---|
| Test Board | Extinguishing Solution Used | Panel Starting Weight | Panel Ending Weight | Weight Loss (g) | Percent Weight Loss | Mean Weight Loss (%) | St. Dev. |
| W1 | Water | 305.0 | 234.4 | 70.6 | 23.1 | 22.92 | 0.003 |
| W2 | Water | 306.6 | 236.0 | 70.6 | 23.0 | | |
| W3 | Water | 305.5 | 236.5 | 69.0 | 22.6 | | |
| S1 | 0.1% Ex. 4 | 306.5 | 242.5 | 64.0 | 20.9 | 20.58 | 0.008 |
| S2 | 0.1% Ex. 4 | 308.2 | 247.2 | 61.0 | 19.8 | | |
| S3 | 0.1% Ex. 4 | 304.7 | 239.2 | 65.1 | 21.4 | | |
| S4 | 0.3% Ex. 4 | 304.2 | 244.4 | 59.8 | 19.7 | 20.30 | .006 |
| S5 | 0.3% Ex. 4 | 296.2 | 235.3 | 61.6 | 20.7 | | |
| S6 | 0.3% Ex. 4 | 299.2 | 237.9 | 61.3 | 20.5 | | |

While the difference in percent weight loss was less dramatic with wetting agent solution when compared to water (Tables 8 and 9), there is a clear reduction in weight loss of those panels treated with the Example 5 solution than those treated with water only. NFPA 18 does not state to what degree the panel weight loss difference must be, just that the boards treated with solution should "exhibit less runoff and weight loss than water". Additionally, it was noted that the extinguishment of the panels was faster and more complete with the wetting agent solutions than with plain water.

Class A Heptane Fire Test

Chapter 7 of NFPA 18 specifies that products listed for use on Class A fires shall pass the single Class B fire extinguishment test. Wetting agent solutions at 3.0% concentration were evaluated to determine their ability to extinguish a Class B heptane fire as follows:

1. A 4.65 m2 (50 ft 2) 20B pan constructed as described in UL 711 is fitted with a backboard that is the width of the pan and 0.9 m (3 ft) high.

2. A 51 mm (2 in.) layer of heptane fuel is floated on a 102 mm (4 in.) depth of water.

3. The fuel in the pan is ignited and allowed to free burn for 60 seconds.

4. A 37.9 L/min (10 gpm) nozzle is used to apply the wetting agent solution to the fire using one, or a combination, of the following methods:

a. The nozzle shall be fixed in position at an angle above the horizontal in order to direct the discharge across the pan onto the backboard for the entire duration of the test; or b. The nozzle shall be permitted to be moved as necessary for control and extinguishment.

5. In no case shall the nozzle extend over any part of the test pan.

6. In order for the test to be successful, the fire shall be extinguished within 5 minutes of the start of application of the wetting agent solution.

A wetting agent is considered to have passed this test if successfully extinguishes the 20B heptane fire on two consecutive attempts.

Results of the Heptane Fire Test

The 3.0% solution of Fire Foam Concentrate of Example 5, successfully and fully extinguished the 20B (50 square foot) heptane fire within 5 minutes of application in two consecutive attempts, which is the passing criteria for this test. No re-ignition occurred after full extinguishment.

Summary of Example 8

The fire foam concentrates of Example 4 and 5 wetting agents were found to be capable of successfully passing all four fire-related tests contained within NFPA 18 (2017 ed.) for Class A extinguishers. This includes extinguishment of wood crib fires, deep-seated fires, wood fiberboard penetration, and the heptane fire test.

Example 9—Preparation of Enzyme Modified Soy Meal

A soy meal was ground to pass through a 200 mesh sieve. A soy meal water dispersion was prepared by adding 69.7 g of the 200 mesh soy meal to 1551.4 g of 40° C. tap water, to which 1 g of sodium sulfite had been added. The mixture became very viscous upon hand mixing with a spatula. To this mixture was added, 5 g of a pH 10 buffer solution comprised of a 2:1 mixture of sodium carbonate and sodium bicarbonate, followed by 4 g of alcalase enzyme (Novozyme). This was allowed to react for 2 hours at a temperature of 40° C. After the 2 hour reaction time, the viscosity of the soy meal dispersion had been sufficiently reduced to be useful in a fire foam concentrate formulation. Finally, 20 g of 1-butanol was added to complete the preparation. This composition was then used to prepare fire foam formulations in the following examples.

Example 10—Preparation of a Fire Foam Concentrate with Capryl Glucoside Non-Ionic Surfactant The enzyme modified soy meal dispersion of Example 9 was used to prepare a fire foam concentrate composition comprising a non-ionic surfactant. In this example, capryl glucoside (CocoJoJo Organic) was diluted from 60% active ingredients (as received) to 30% active. To 35 g of the modified soy meal dispersion from Example 9, was added 15.0 g of the 30% capryl glucoside, followed by 0.2 g of citric acid. This was mixed thoroughly to a uniform dispersion.

Example 11—Preparation of a Fire Foam Concentrate with Decyl Glucoside Non-Ionic Surfactant The enzyme modified soy meal dispersion of Example 9 was used to prepare a fire foam concentrate composition comprising a non-ionic surfactant. In this example, decyl glucoside (CocoJoJo Organic) was diluted from 55% active ingredients (as received) to 30% active. To 35 g of the modified soy meal dispersion from Example 9, was added 15.0 g of the 30% decyl glucoside, followed by 0.2 g of citric acid. This was mixed thoroughly to a uniform dispersion.

Example 12—Laboratory Evaluation of Examples 10 and 11 Fire Foam Concentrate for Wetting Ability The soy-based fire foam concentrates from Examples 10 and 11 were diluted to 0.2% with normal tap water and placed in a plastic vessel capable of delivering a uniform droplet size. Tap water was used as the control in the evaluation and also placed in a plastic vessel capable of delivering a uniform droplet size. Strips of pine board measuring 2 inches by 1 inch and ⅛ inch thickness, was sanded with 400 grit sandpaper to a smooth finish. Three drops of the water or test liquids were added to the pine boards and a timer was started. The time was recorded from when the droplet was placed on the board, to the time where the droplet was completely soaked into the board. The average time of the three drops was recorded to the nearest 15 seconds, with the results summarized in Table 10.

TABLE 10

| Sample | Tap Water | Example 10 | Example 11 |
|---|---|---|---|
| Time | 14 min 45 secs | 4 min 15 secs | 4 min 30 secs |

From the results above, it is determined that the compositions of Examples 10 and 11 substantially reduced the absorption time (wetting ability) into pine wood thereby demonstrating its applicability of a Class A wetting agent.

Example 13-Laboratory Foam Evaluation of Fire Foam Formulations Using Ocean Water Dilution The foam concentrates prepared in Example 1, 10, and 11, were evaluated for foaming properties by adding 2 g of the foam concentrates to 198 g of room temperature ocean water (PetSmart) in an 900 ml stainless steel Hamilton Beach mixing beaker. The Hamilton Beach mixer was set to speed setting 1, and the beaker was attached to the mixer and mixing begun. A stop watch measured the time it took for the generated foam to reach to full capacity of the 800 ml beaker (4× volume), with the results summarized in Table 11.

TABLE 11

| Sample | Ex 1 Fresh | Ex 1 Ocean | Ex 10 Fresh | Ex 10 Ocean | Ex 11 Fresh | Ex 11 Ocean |
|---|---|---|---|---|---|---|
| Time (secs) | 13 | 29 | 35 | 42 | 45 | 54 |

The results recorded in Table 11 demonstrate that while the use of non-ionic surfactants to produce the fire foam concentrates of Examples 10 and 11 were not as fast foaming to the 4× volume compared to the surfactant mixture used in Example 1, there is demonstrated utility in ocean water dilution applications as shown by the slight increase in time to foam as compared to the fire foam concentrate of Example 1 where the time to foam was doubled when diluting with ocean water.

Methods of Use

Figure 2:
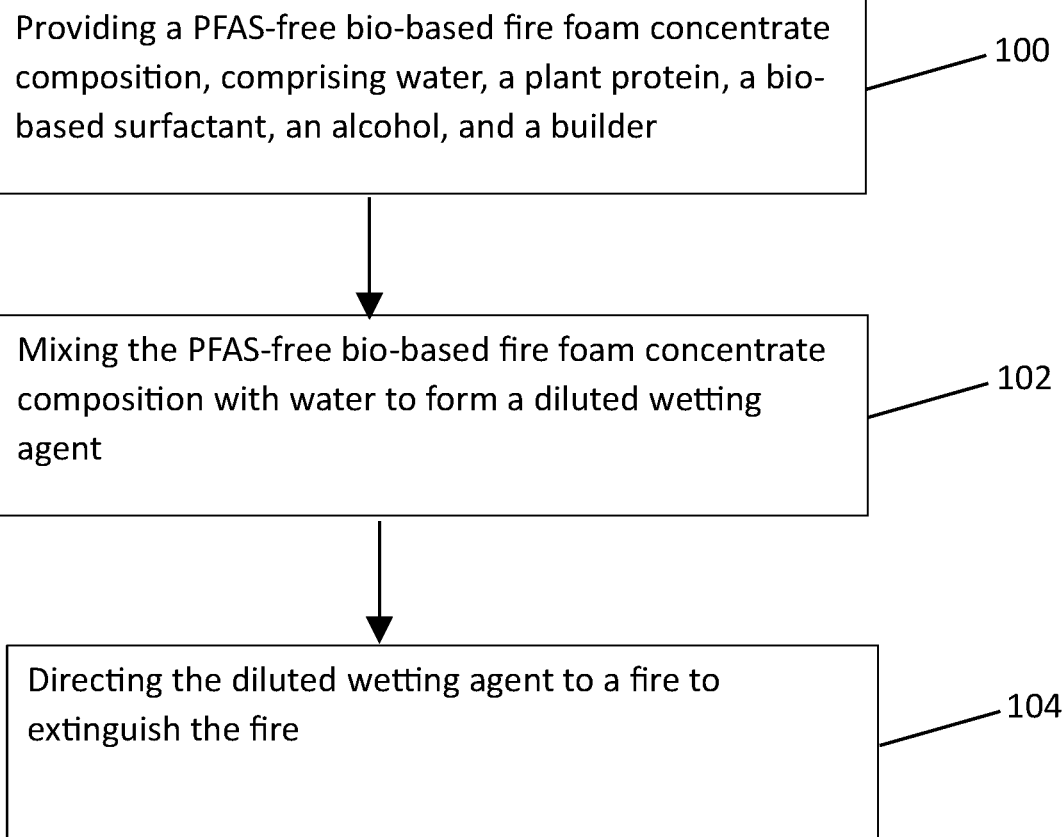
FIG. 2 shows first method of extinguishing a fire using a PFAS-free bio-based fire foam concentrate composition.

A method of extinguishing a fire using a PFAS-free bio-based fire foam concentrate composition as described above can be used to extinguish fires. In a first embodiment as outlined in FIG. 2, the method includes: (100) providing a PFAS-free bio-based fire foam concentrate composition, comprising water, a plant protein, a bio-based surfactant, an alcohol, and a builder; (102) mixing the PFAS-free bio-based fire foam concentrate composition with water to form a diluted wetting agent; and (103) directing the diluted wetting agent to a fire to extinguish the fire. Preferably, the plant protein used is a plant protein consisting essentially of a soy-based protein. Preferably, the plant protein used has been chemically or enzymatically modified. More preferably, the plant protein used has been modified with a protease enzyme. In a preferred embodiment, the plant protein used is a protein consisting essentially of a soy-based protein and has been modified with a protease enzyme to a Brookfield viscosity of less than 2000 cps utilizing spindle #4 at 100 rpm at 40° C. Preferably, the plant protein used is a protein consisting essentially of a soy-based protein and has been modified with a protease enzyme, and the composition preferably includes from about 20% to about 80% of soy-based based on the total dry weight of the composition. More preferably, the composition used preferably includes from about 50% to about 70% of soy-based based on the total dry weight of the composition.

Another method of extinguishing a fire using a PFAS-free bio-based fire foam concentrate composition as described above can be used to extinguish fires. In this second embodiment as outlined in FIG. 3, the method includes: (200) providing a PFAS-free bio-based fire foam concentrate composition, comprising water, an extracted and flash desolventized soy-based protein flour, a bio-based surfactant, an alcohol, and a builder; (202) mixing the PFAS-free bio-based fire foam concentrate composition with water to form a diluted wetting agent; (204) directing the diluted wetting agent to a fire to extinguish the fire. Preferably, the soy-based protein flour used has been chemically or enzymatically modified. More preferably, the soy-based protein flour used has been modified with a protease enzyme. Preferably, the soy-based protein flour used has been modified with a protease enzyme to a Brookfield viscosity of less than 2000 cps utilizing spindle #4 at 100 rpm at 40° C. In a preferred embodiment, the soy-based protein flour used has been modified with a protease enzyme and the composition used includes from about 20% to about 80% of soy-based protein flour based on the total dry weight of the composition. More preferably, the composition used includes from about 50% to about 70% of soy-based protein flour based on the total dry weight of the composition.

Figure 4:
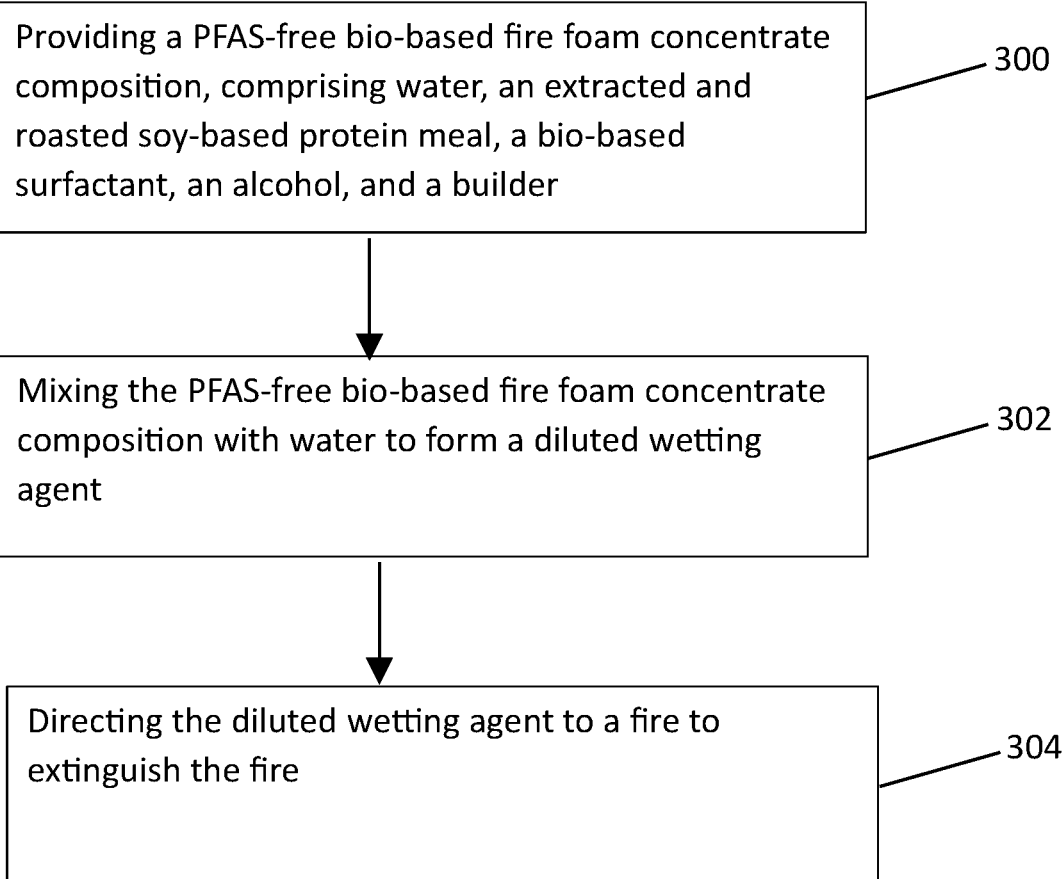
FIG. 4 shows a third method of extinguishing a fire using a PFAS-free bio-based fire foam concentrate composition.

Another method of extinguishing a fire using a PFAS-free bio-based fire foam concentrate composition as described above can be used to extinguish fires. In this third embodiment as outlined in FIG. 4, the method includes (300) providing a PFAS-free bio-based fire foam concentrate composition, comprising: water, an extracted, and roasted soy-based protein meal, a bio-based surfactant, an alcohol, and a builder; (302) mixing the PFAS-free bio-based fire foam concentrate composition with water to form a diluted wetting agent; and (304) directing the diluted wetting agent to a fire to extinguish the fire. Preferably, the soy-based protein meal used has been chemically or enzymatically modified. More preferably, the soy-based protein meal used has been modified with a protease enzyme. In a preferred embodiment, the soy-based protein meal used has been modified with a protease enzyme to a Brookfield viscosity of less than 2000 cps utilizing spindle #4 at 100 rpm at 40° C. In a preferred embodiment, the soy-based protein meal used has been modified with a protease enzyme and the composition used includes from about 20% to about 80% of soy-based protein meal based on the total dry weight of the composition. More preferably, the composition used includes from about 50% to about 70% of soy-based protein meal based on the total dry weight of the composition.

Yet another method of extinguishing a fire using a PFAS-free bio-based fire foam concentrate composition as described above can be used to extinguish fires. In this fourth embodiment as outlined in FIG. 5, the method includes (400) providing a PFAS-free bio-based fire foam concentrate composition with a bio-based content of greater than 80% on a dry weight basis, the composition comprising a soy protein flour or meal that has been enzymatically modified with a protease enzyme to a viscosity of less than 2000 cps utilizing spindle #4 at 100 rpm at 40° C., a mixture of CAPB and SLS surfactants, 1-biobutanol, and a citric acid builder; (402) mixing the PFAS-free bio-based fire foam concentrate composition with water to form a diluted wetting agent; and (404) directing the diluted wetting agent to a fire to extinguish the fire.

The disclosure has been described with reference to various specific and illustrative embodiments and techniques. However, one skilled in the art will recognize that many variations and modifications may be made while remaining within the spirit and scope of the disclosure. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method of extinguishing a fire using a PFAS-free bio-based fire foam concentrate composition, the method comprising:

providing a PFAS-free bio-based fire foam concentrate composition, comprising: water, an enzymatically modified plant protein that has been prepared by:

forming a protein dispersion by mixing the plant protein with water containing 0.1% to 1% sodium bisulfite or sodium sulfite based on a dry weight of the plant protein, adjusting the protein dispersion to pH 7-8 by adding a buffer comprising a 2:1 mixture of sodium carbonate and sodium bicarbonate, modifying the plant protein in the plant dispersion with an alcalase enzyme at a concentration sufficient to substantially reduce the viscosity of the protein dispersion for 1-2 hours at a temperature between 30 degrees C. and 50 degrees C., and adding a C1-C4 alcohol to halt the enzymatic reaction;

a non-ionic surfactant selected from capryl glucoside and decyl glucoside, the C1-C4 alcohol, and a builder;

mixing the PFAS-free bio-based fire foam concentrate composition with water to form a diluted wetting agent;

directing the diluted wetting agent to a fire to extinguish the fire.

2. The method according to claim 1 wherein the plant protein is a plant protein comprising a soy-based protein.

3. The method according to claim 1, wherein modification of the plant protein results in the concentrate composition having a Brookfield viscosity of less than 2000 cps utilizing spindle #4 at 100 rpm at 40° C.

4. The method according to claim 1, wherein the composition is a composition comprising from about 20% to about 80% of the plant protein based on the total dry weight of the composition.

5. The method according to claim 1, wherein the composition is a composition comprising from about 50% to about 70% of the plant protein based on the total dry weight of the composition.

6. A method of extinguishing a fire using a PFAS-free bio-based fire foam concentrate composition, the method comprising:

providing a PFAS-free bio-based fire foam concentrate composition, comprising: water, an extracted and flash desolventized soy-based protein flour that has been prepared by:

forming a protein dispersion by mixing the soy-based protein flour with water containing 0.1% to 1% sodium bisulfite or sodium sulfite based on the dry weight of the soy-based protein flour, adjusting the protein dispersion to pH 7-8 by adding a buffer comprising a 2:1 mixture of sodium carbonate and sodium bicarbonate, enzymatically modifying the soy-based protein flour in the protein dispersion with an alcalase enzyme at a concentration sufficient to substantially reduce the viscosity of the protein dispersion for 1-2 hours at a temperature between 30 degrees C. and 50 degrees C., and adding a C1-C4 alcohol to halt the enzymatic reaction;

a non-ionic surfactant selected from capryl glucoside and decyl glucoside, the C1-C4 alcohol, and a builder;

mixing the PFAS-free bio-based fire foam concentrate composition with water to form a diluted wetting agent;

directing the diluted wetting agent to a fire to extinguish the fire.

7. The method according to claim 6, wherein the modification of the soy-based protein flour results in the concentrate composition having a Brookfield viscosity of less than 2000 cps utilizing spindle #4 at 100 rpm at 40° C.

8. The method according to claim 6, wherein the composition is a composition comprising from about 20% to about 80% of the soy-based protein flour based on the total dry weight of the composition.

9. The method according to claim 6, wherein the composition is a composition comprising from about 50% to about 70% of the soy-based protein flour based on the total dry weight of the composition.

* * * * *